(12) United States Patent
Cantor

(10) Patent No.: US 6,524,788 B1
(45) Date of Patent: Feb. 25, 2003

(54) METHODS FOR MONITORING AND GUIDING THERAPEUTIC SUPPRESSION OF PARATHYROID HORMONE IN RENAL PATIENTS HAVING SECONDARY HYPERPARATHYROIDISM

(76) Inventor: Thomas L. Cantor, 11149 Shining Light Way, El Cajon, CA (US) 92020

( * ) Notice: Subject to any disclaimer, the term of this patent is extended or adjusted under 35 U.S.C. 154(b) by 0 days.

(21) Appl. No.: 10/002,818

(22) Filed: Nov. 2, 2001

(51) Int. Cl.[7] .......................... C12Q 1/00; G01N 33/53; A61K 31/59; A61K 33/06
(52) U.S. Cl. .......................... 435/4; 435/7.1; 514/167; 424/682
(58) Field of Search ...................... 435/4, 7.1; 436/500; 530/300; 424/602, 682; 514/1, 167

(56) References Cited

U.S. PATENT DOCUMENTS

| | | | |
|---|---|---|---|
| 4,369,138 A | 1/1983 | Lindall | 260/112.5 |
| 4,423,037 A | 12/1983 | Rosenblatt et al. | 424/177 |
| 4,508,828 A | 4/1985 | Lindall et al. | 436/500 |
| 4,656,250 A | 4/1987 | Morita et al. | 530/324 |
| 6,030,790 A | 2/2000 | Adermann et al. | 435/7.1 |

FOREIGN PATENT DOCUMENTS

| | | |
|---|---|---|
| DE | 33 47 548 | 7/1985 |
| DE | 44 34 551 | 4/1996 |
| EP | 0 783 522 | 12/2001 |
| WO | WO 91/06564 | 5/1991 |
| WO | WO 93/06845 | 4/1993 |
| WO | WO 94/03201 | 2/1994 |
| WO | WO 96/10041 | 4/1996 |

OTHER PUBLICATIONS

Adermann et al., Innovations and Perspectives in Solid Phase Synthesis, Epton (ed.), Mayflower World Wide, Birmingham (1994) pp. 429–432.
Atkinson et al., Journal of Immunoassay (1982) 3(1):31–51.
Blind et al., Clin. Chem. (1987) 33(8):1376–1381.
Bowie et al., Science (1990) 247:1306–1310.
Brossard et al., Journal of Clinical Endocrinology and Metabolism (1996) 81(11):3923–3929.
Campbell, Monoclonal Antibody and Immunosensor Technology, in Laboratory Techniques in Biochemistry and Molecular Biology, van der Vliet (ed.), Elsevier (1991) pp. 1–11,42–45.
Caporale and Rosenblatt, Paraththyroid Hormone Antagonists Effective in vivo, in: Advances in Experimental Medicine and Biology, New York (1986) pp. 315–327.
Clinical Chemistry (1999) 45(6)Suppl:A97b, Abstract Nos. 339–341.
D'Amour et al., Am. J. Physiol. (1986) 251:E680–E687.
Daniel et al., Virology (1994) 202:540–549.
Divieti, P. et al. (2001). J. Bone Miner Res 2001:Suppl 1, S307.

Faugere, M.C. et al. (2001). Kidney International 60:1460–1468.
Faugere, M.C. et al. Nephrology, Bone& Mineral Metabolism A3995.
Fischer et al., The Journal of Clinical Investigation (1974) 54:1382–1394.
Gao et al., Clinica Chimica Acta (1996) 245:39–59.
Goodman, W. et al. (2000). NEJM 342:20, 1478–1483.
Gordon et al., Parathyroid Hormone Domain for Protein Kinase C Stimulation Located within Amphiphilic Helix, in: Peptides: Chemistry and Biology, Proceedings of the Twelfth American Peptide Symposium, Jun. 16–21, 1991, Cambridge, MA, Smith and Rivier (eds.) Escom Science Publishers (1992) pp. 37–39.
Hashimoto et al., Journal of Cardiovascular Pharmacology (1981) 3(4):668–676.
Hehrmann et al., Journal of Immunoassay (1980) 1(2):151–174.
John et al., Journal of Clinical Endocrinology and Metabolism (1999) 84(11):4287–4290.
LePage et al., Clin. Chem. (1998) 44:805–810.
Logue et al., Journal of Immunological Methods (1991) 137:159–166.
Mägerlein et al., Arzneim.–Forsch./Drug Res. (1998) 48(1):197–204.
Mägerlein et al., Arzneim.–Forsch./Drug Res. (1998) 48(II):783–787.
Mallette, Journal of Clinical Endocrinology and Metabolism (1980) 50(1):201–203.
Nakamura et al., Endocrinol. JPN (1981) 28(4):547–549.
Ngo et al., The Protein Folding Problem and Tertiary Structure Prediction, Merz et al., (eds.), Birkhäuser Boston (1994) pp. 492–495.
Niall et al., Proc. Natl. Acad. Sci. USA (1974) 71(2):384–388.
Nussbaum et al., Chemical Abstracts (1982) 96(5):181–192.
Pang et al., Pharmacol. Exp. Ther. (1981) 216(3):567–571.
Qi et al., Am. J. Kidney Dis. (1995) 26:622–631.
Quarles et al., J. Clin. Endocrinol. Metab. (1992) 75:145–150.

(List continued on next page.)

*Primary Examiner*—Elizabeth Kemmerer
*Assistant Examiner*—Ruixiang Li
(74) *Attorney, Agent, or Firm*—Morrison & Foerster LLP

(57) ABSTRACT

The present invention relates to novel methods for monitoring and guiding therapeutic suppression of parathyroid hormone in renal patients having secondary hyperparathyroidism. One determines and monitors the level of cyclase activating parathyroid hormone and cyclase inactive parathyroid hormone in the renal patient. The parathyroid hormone suppressing therapeutic is administered to the patient so as to minimize the level of cyclase inactive parathyroid hormone.

25 Claims, 2 Drawing Sheets

OTHER PUBLICATIONS

Stadler, Homologous Radioimmunoassay for Human Parathyroid Hormone (Residues 1–34) with Biotinylated Peptide as Tracer, in Calcium Regulating Hormones, Vitamin D Metabolites, and Cyclic AMP Assays and their Clinical Application, Schmidt–Gayk et al., (eds.), Berlin/Heidelberg, Springer, (1990) pp. 137–150.

Tampe et al., J. Immunoassay (1992) 13(1):1–13.

Visser et al., Acta Endocrinology (1979) 90:90–102.

Wingender et al., Structure–Function Relationship in Parathyroid Hormone in: Advances in Protein Design, International Workshop, Blöcker et al., (eds.), VCH (1988) pp. 167–176.

Zanelli et al., Journal of Immunoassay (1983) 4(2):175–206.

Zemplar package insert, Abbott Reference (1998). 06–9998–R1–Rev. Roche Laboratories.

Whole Human PTH (1-84)

METHODS FOR MONITORING AND GUIDING THERAPEUTIC SUPPRESSION OF PARATHYROID HORMONE IN RENAL PATIENTS HAVING SECONDARY HYPERPARATHYROIDISM

TECHNICAL FIELD

The present invention relates to novel methods for monitoring and guiding therapeutic suppression of parathyroid hormone in renal patients having secondary hyperparathyroidism. One determines and monitors the level of cyclase activating parathyroid hormone and cyclase inactive parathyroid hormone in the renal patient. The parathyroid hormone suppressing therapeutic is administered to the patient so as to minimize the level of cyclase inactive parathyroid hormone.

BACKGROUND ART

Calcium plays an indispensable role in cell permeability, the formation of bones and teeth, blood coagulation, transmission of nerve impulse, and normal muscle contraction. The concentration of calcium ions in the blood is, along with calcitrol and calcitonin, regulated mainly by parathyroid hormone (PTH). Although calcium intake and excretion may vary, PTH serves through a feedback mechanism to maintain a steady concentration of calcium in cells and surrounding fluids. When serum calcium lowers, the parathyroid glands secrete PTH, affecting the release of stored calcium. When serum calcium increases, stored calcium release is retarded through lowered secretions of PTH.

The complete form of human PTH, sometimes referred to in the art as hPTH but referred to in the present invention as cyclase activating PTH or whole PTH, is a unique 84 amino acid peptide (SEQ ID NO.1), as is shown in FIG. 1. Researchers have found that this peptide has an anabolic effect on bone that involves a domain for protein kinase C activation (amino acid residues 28 to 34) as well as a domain for adenylate cyclase activation (amino acid residues 1 to 7). However, various catabolic forms of clipped or fragmented PTH peptides also are found in circulation, most likely formed by intraglandular or peripheral metabolism. For example, whole PTH can be cleaved between amino acids 34 and 35 to produce a (1–34) PTH N-terminal fragment and a (35–84) PTH C-terminal fragment. Likewise, clipping can occur between either amino acids 36 and 37 or 37 and 38. Recently, a large PTH fragment referred to as "non-(1–84) PTH" has been disclosed which is clipped closer to the N-terminal end of PTH. (See R. LePage et alia, "*A non-(1–84) circulating parathyroid hormone (PTH) fragment interferes significantly with intact PTH commercial assay measurements in uremic samples*" Clin Chem (1998); 44: 805–810.)

The clinical need for accurate measurement of PTH is well demonstrated. Serum PTH level is one of the most important indices for patients with the following diseases: familial hypocalciuria; hypercalcemia; multiple endocrine neoplasia types I and II; osteoporosis; Paget's bone disease; primary hyperparathyroidism—caused by primary hyperplasia or adenoma of the parathyroid glands; pseudohypoparathyroidism; and renal failure, which can cause secondary hyperparathyroidism.

PTH plays a role in the course of disease in a patient with chronic renal failure. Renal osteodystrophy (RO) is a complex skeletal disease comprising osteitis fibrosa cystica (caused by PTH excess), osteomalacia—unmineralized bone matrix (caused by vitamin D deficiency), extraskeletal calcification/ossification (caused by abnormal calcium and phosphorus metabolism), and adynamic low bone turnover disease (contributed to by PTH suppression). Chronic renal failure patients can develop RO. Failing kidneys increase serum phosphorus hyperphosphoremia) and decrease 1,25-dihydroxyvitamin D (1,25-D) production by the kidney. The former results in secondary hyperparathyroidism from decreased gastrointestinal calcium absorption and osteitis fibrosa cystica from increased PTH in response to an increase in serum phosphorus. The later causes hypocalcemia and osteomalacia. With the onset of secondary hyperparathyroidism, the parathyroid gland becomes less responsive to its hormonal regulators because of decreased expression of its calcium and vitamin D receptors. Serum calcium drops. RO can lead to digital gangrene, bone pain, bone fractures, and muscle weakness.

For chronic renal failure patients with secondary hyperparathyroidism, a number of different therapeutic treatments are available. One can administer calcium carbonate so as to directly adjust the available calcium ion level. However, with the increasing incidence of ectopoic calcification, increasing calcium intake is often not desirable. One can administer calcimimetics, such as AMG073 made by Amgen, Inc. of Thousand Oaks, Calif. However, AMG073 has been shown to have some hypercalcemic effect and has not been approved for use in the USA. One can administer vitamin D analogues, (such as the Calcijex or Zemplar brands made by Abbott Labs of Abbott Park, Ill. or the Rocaltrol brand made by Roche Laboratories of Basle, Switzerland), so as to lower PTH. However, researchers have found that vitamin D analogues can oversuppress PTH, thereby leading to adynamic low bone turnover disease setting the patient at risk of ectopic and vascular calcification. (See the package insert for Zemplar, Abbott Reference 06-9998-R1-Rev, April 1998. See the package insert for Rocaltrol, Roche Laboratories, inc. November 1998 Product identification Guide, page 334.)

Researchers have also found that a large circulating PTH fragment (cyclase inactive parathyroid hormone) functions as a naturally occurring PTH antagonist. Cyclase inactive PTH has been found to be useful, alongside whole PTH, as an indicator in separating untreated end stage renal disease (ESRD) patients with high bone turnover from those with adynamic low bone turnover. (See Faugere, M. C. et alia. "*Improved Assessment of Bone Turnover by the PTH 1–84/largeC-PTH fragments ratio in ESRD patients*", Kidney International 2001; 60: 1460–1468.) Moreover, researchers have found that cyclase inactive PTH can cause adynamic low bone turnover by inhibiting the formation of osteoclasts, bone resorption, and bone turnover. (See Divieti P. et alia, "*In vitro Inhibition of Bone Resorption by Human PTH (7–84)*" J. Bone Miner Res 2001:Suppl 1, S307. See also Faugere, M. C. et alia, "*The Effects of PTH (1–84) on bone turnover are Antagonized by PTH (7–84) in Thyroparathyroidectomized and Nephrectomized Rats*"; J Am Soc Nephrol 12:2001, 764A.)

Determining circulating biologically active PTH levels in humans has been challenging. One major problem is that PTH is found at low levels, normally 10 pg/mL to 65 pg/mL. Coupled with extremely low circulating levels is the problem of the heterogeneity of PTH and its many circulating fragments. In many cases, immunoassays have faced substantial and significant interference from circulating PTH fragments. For example, some commercially available PTH kits have almost 100% cross-reactivity with the non-(1–84) PTH fragment, (see the LePage article).

PTH immunoassays have varied over the years. One early approach is a double antibody precipitation immunoassay found in U.S. Pat. No. 4,369,138 to Arnold W. Lindall et alia. A first antibody has a high affinity for a (65–84) PTH fragment. A radioactive labeled (65–84) PTH peptide is added to the sample with the first antibody to compete for the endogenous unlabeled peptide. A second antibody is added which binds to any first antibody and radioactive labeled PTH fragment complex, thereby forming a precipitate. Both precipitate and supernatant can be measured for radioactive activity, and endogenous PTH levels can be calculated therefrom.

In an effort to overcome PTH fragment interference, immunoradiometric two-site assays for intact PTH (I-PTH) have been introduced, such as Allegro® Intact PTH assay by the Nichol's Institute of San Juan Capistrano, Calif. In one version, a capture antibody specifically binds to the C-terminal portion of hPTH while a labeled antibody specifically binds to the N-terminal portion of the captured hPTH. In another, two monoclonal antibodies were used, both of which attached to the N-terminal portion of hPTH. Unfortunately, these assays have problems in that they measure but do not discriminate between whole PTH and non-whole PTH peptide fragments. This inability comes to the fore in hyperparathyroid patients and renal failure patients who have significant endogenous concentrations of large, non-whole PTH fragments.

Recently, Scantibodies Laboratory, Inc. of Santee, Calif. USA introduced a series of novel kits that allow for the accurate measurement of both cyclase activating PTH and cyclase inactive PTH, (a large, non-whole PTH peptide fragment having an amino acid sequence from between (SEQ ID No.2 [$PTH_{2-84}$]) and (SEQ ID No.3 [$PTH_{34-84}$]). The cyclase activating PTH assay is a direct measurement, while the cyclase inactive PTH assay is a calculated value from the difference of the cyclase activating PTH assay value and a total PTH (both cyclase activating PTH and cyclase inactive PTH) assay value. A number of unexpected advantages have become available to the physician, including the first non-invasive method for assisting in the differentiation of secondary hyperparathyroid patients with HBT and ALBT.

DISCLOSURE OF THE INVENTION

The present invention relates to novel methods for monitoring and guiding therapeutic suppression of parathyroid hormone in renal patients having secondary hyperparathyroidism. One determines and monitors the level of cyclase activating parathyroid hormone and cyclase inactive parathyroid hormone in the renal patient. The parathyroid hormone suppressing therapeutic is administered to the patient so as to minimize the level of cyclase inactive parathyroid hormone.

Secondary hyperparathyroidism is a common disease in renal compromised patients, especially those with ESRD. Virtually all ESRD patients have bone disease and mineral metabolism disorders, either high bone turnover disease or adynamic low bone turnover disease. Elevated levels of whole PTH (with respect to cyclase inactive PTH) lead to high bone turnover disease (HBT). Elevated levels of cyclase inactive PTH (with respect to whole PTH) lead to adynamic low bone turnover disease (ALBT). The more serious of the two is ALBT. Ectopic tissue calcification results in vascular stenosis (including occlusion of coronary arteries) and aortic rigidity. ALBT patients are more likely to die due to a circulatory system failure, such as myocardial infarction than those with HBT. One reason is the difficulty in finding a reliable therapeutic indicator for ALBT or for therapeutic oversuppression that leads to ALBT. Another reason is that due to the lack of the reliable indicator, whole PTH suppressant therapy can inadvertently lead to ALBT due to PTH oversuppression. Difficulty with implementing this therapy can be seen in the setting of at least ten different PTH target recommendations within the past decade. The net result of this uncertainty in therapeutic indicators is that the incidence of vascular calcification has been reported to be 88% for ESRD patients, leading to a slow and agonizing death. (See Goodman, W. et alia, "*Coronary Artery Calcification in Young Adults with End Stage Renal Disease Who Are Undergoing Dialysis*"; NEJM 2000, May 18; 342:20, 1478–1483.)

A novel finding of the present invention is that while whole PTH only decreases in response to the administration of whole PTH suppressants, cyclase inactive PTH does not. For an untreated renal patient with an elevated whole PTH, the administration of a PTH suppressant will also suppress cyclase inactive PTH initially. However, as the PTH suppressant dosage increases, the level of cyclase inactive PTH will reach a minimal level and then start to increase before the level of whole PTH stops decreasing. So as to avoid inducing ALBT in such patients, the administration of PTH suppressant should be adjusted so as to stay about that minimal cyclase inactive PTH level. Ordinarily skilled artisans know that this level may vary from patient to patient, but can determine what is best for a particular patient through monitoring the response to therapy.

Preferably, whole PTH is measured directly using an assay that does not detect cyclase inactive PTH either in blood, plasma, or serum. Scantibodies Laboratory, Inc. of Santee, Calif. makes such an assay.

Cyclase inactive PTH should be measured using an assay that either directly detects cyclase inactive PTH (but not whole PTH) or indirectly through a total PTH measurement. An indirect measurement subtracts the whole PTH value from the total PTH value, deriving the cyclase inactive PTH value. Thus, one should use a total PTH assay that is designed to have essentially 100% cross-reactivivity with cyclase inactive PTH. Scantibodies Laboratory, Inc. of Santee, Calif. makes such an assay.

A novel finding of the present invention is that while whole PTH only decreases in response to the administration of whole PTH suppressants, cyclase inactive PTH does not. For an untreated renal patient with an elevated whole PTH, the administration of a PTH suppressant will also suppress cyclase inactive PTH initially. However, as the PTH suppressant dosage increases, the level of cyclase inactive PTH will reach a minimal level and then start to increase before the level of whole PTH stops decreasing. So as to avoid inducing ALBT in such patients, the administration of PTH suppressant should be adjusted so as to stay about that minimal cyclase inactive PTH level. Ordinarily skilled artisans know that this level may vary from patient to patient, but can determine what is best for a particular patient through monitoring the response to therapy.

BEST MODES FOR CARRYING OUT THE INVENTION

A clinical trial was held for ninety ESRD patients. Each patient had been receiving vitamin D suppressant therapy in accordance with the manufacturer's guidelines. Each patient was removed from the therapy for a washout period of four weeks, and this was confirmed by a rise in PTH measurements after removal of the therapeutic. PTH maxacalcitol (made by Chugai Pharmaceutical Corporation of Tokyo, Japan) suppressant therapy was started after the washout at a constant administration of 5.5 μg intravenously every three days. Blood samples were obtained from each patient after the washout (week 0), six weeks after therapy restart (week 6), and twelve weeks after therapy restart (week 12). The samples were assayed for whole PTH and cyclase inactive PTH using the whole PTH assay and total PTH assay made by Scantibodies Laboratory, Inc. The samples were assayed for bone specific alkaline phosphatase using a commercially available immunoassay from Hybritech, Inc. of San Diego, Calif.

Clinical Results

Figure 1:
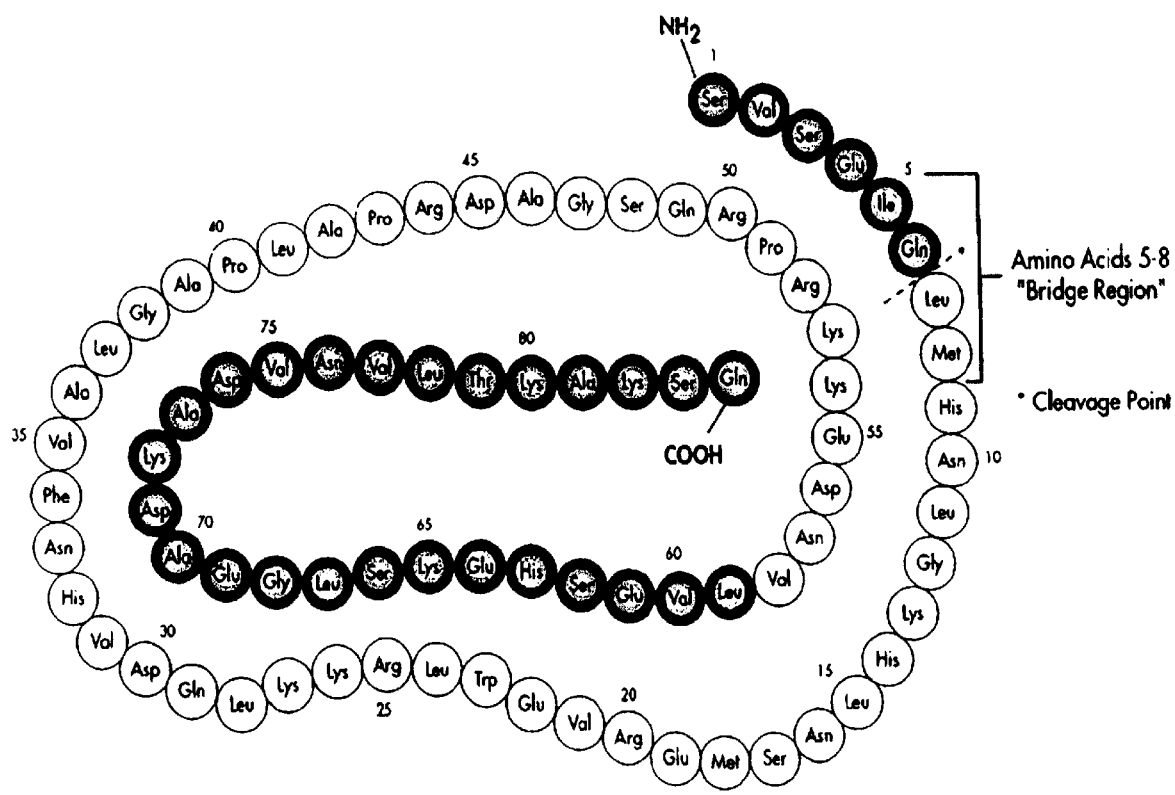
FIG. 1 is a diagrammatic view of human wPTH SEQ ID NO: 1.
Figure 2:
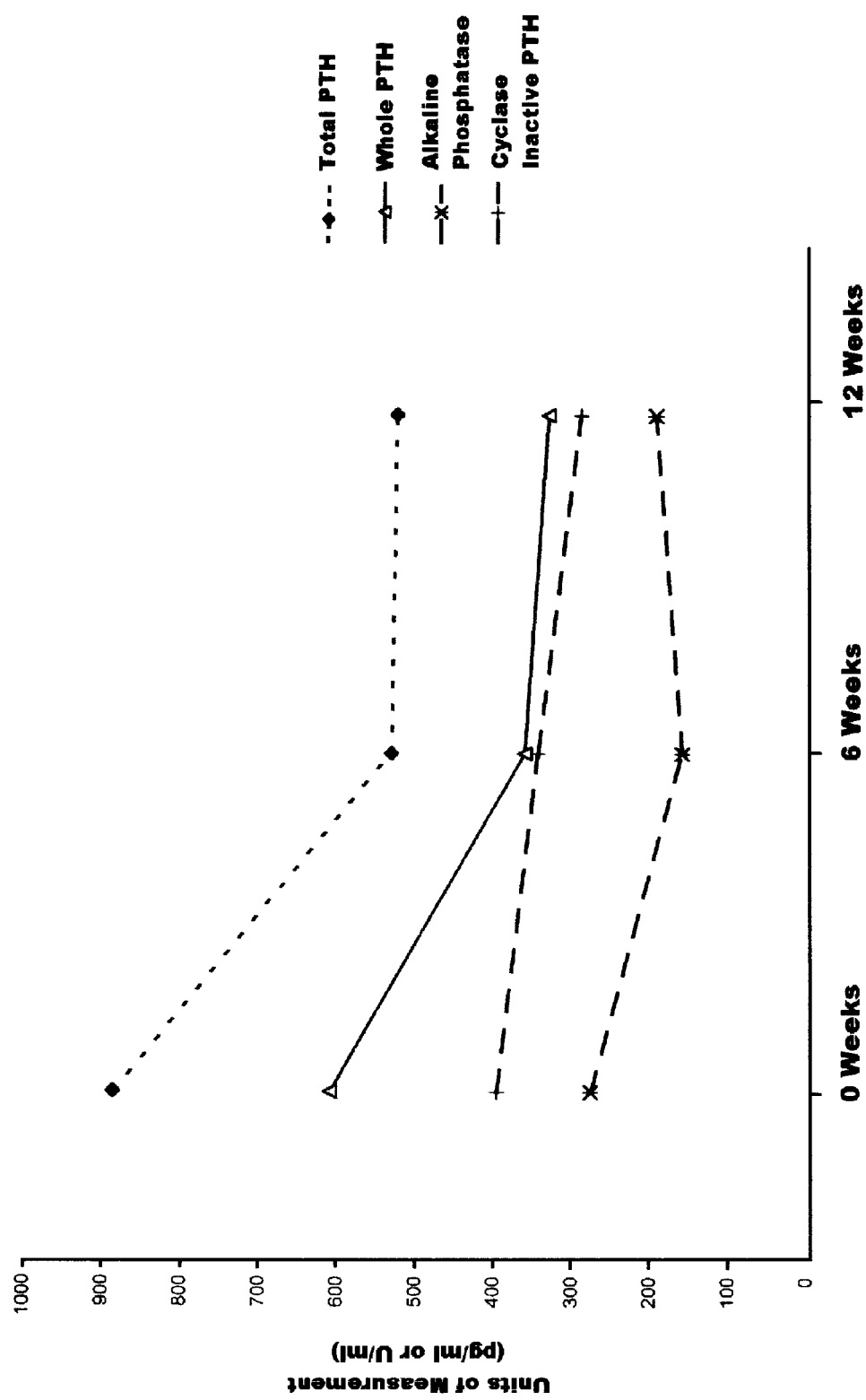
FIG. 2 is a graph comparing PTH measurement parameters over time for patients receiving a PTH suppressant therapy.

The results of the assays for the ninety patients are shown in FIG. 2 and the following table as median values:

TABLE

| Parameter | Time 0 Weeks | Time 6 weeks | Time 12 weeks |
| --- | --- | --- | --- |
| Total PTH pg/ml | 886 | 531 (41% decrease) | 525 (1% decrease) |
| Whole PTH pg/ml | 609 | 361 (41% decrease) | 331 (8% decrease) |
| Cyclase Inactive PTH -pg/ml | 276 | 160 (42% decrease) | 194 (21% increase) |
| Alkaline Phosphatase U/ml | 396 | 344 (13% decrease) | 290 (16% decrease) |

The Table shows how the PTH suppressant lowered both the whole PTH and the total PTH values. After six weeks, these values have fallen 41%. However, after twelve weeks, these values have fallen, respectively 8% and 0.8%. These levels are still commonly regarded as being above normal levels of less than 37 pg/ml for whole PTH and less than 65 pg/ml for total PTH for non-ESRD patients. To the physician, the PTH suppressant is having a hard time driving whole PTH down any further.

The Table also shows the difference in response of cyclase inactive PTH to the PTH suppressant. After six weeks, the value has fallen 42%, responding similarly as whole PTH. However, after twelve weeks, the value rises by 21%, unlike whole PTH. The continued use of PTH suppressant at this level will elevate the cyclase inactive PTH, and, over time, will lead to ALBT and subsequent vascular calcification, as confirmed by the further drop in alkaline phosphatase at twelve weeks. These patients need to have the PTH suppressant dosage lowered so as to maintain the cyclase inactive PTH at a minimal (in this case 160 pg/ml) level. The benefit in reducing whole PTH another 1% is far outweighed by the harm in elevating cyclase inactive PTH, thereby causing ALBT by inhibiting osteoclast formation, a necessary component in healthy bone modeling involving bone resorption and bone turnover.

The ordinarily skilled artisan can appreciate that the present invention can incorporate any number of the preferred features described above.

All publications or unpublished patent applications mentioned herein are hereby incorporated by reference thereto.

Other embodiments of the present invention are not presented here which are obvious to those of ordinary skill in the art, now or during the term of any patent issuing from this patent specification, and thus, are within the spirit and scope of the present invention.

I claim:

1. A method for monitoring and guiding therapeutic suppression of parathyroid hormone in renal patients having secondary hyperparathyroidism comprising:
   a) determining and monitoring the level of cyclase activating parathyroid hormone in a renal patient having secondary hyperparathyroidism;
   b) determining and monitoring the level of cyclase inactive parathyroid hormone in the patient; and
   c) administering a therapeutic to the patient that suppresses cyclase activating parathyroid hormone whereby the amount of therapeutic administered is adjusted such that the level of cyclase inactive parathyroid hormone is minimized.

2. The method of claim 1 wherein the therapeutic is administered in increasing increments from a nominal amount.

3. The method of claim 1 wherein the patient is already receiving the therapeutic, also comprising terminating the therapeutic administration for a time sufficient to allow the patient to return to at least a relatively non-suppressed state.

4. The method of claim 1 wherein the patient is already receiving the therapeutic, also comprising adjusting the amount of therapeutic until the level of cyclase inactive hormone is minimized.

5. The method of claim 1 wherein the therapeutic administration is selected from the group comprising calcium administration, vitamin D analogue administration, and calcimimetic administration.

6. The method of claim 1 wherein steps a) and b) are performed using a sample obtained from a renal patient.

7. The method of claim 6 wherein the sample is selected from the group consisting of a serum, a plasma and a blood sample.

8. The method of claim 1, wherein the cyclase activating parathyroid hormone level is compared with the cyclase inactive parathyroid hormone level.

9. The method of claim 1, wherein the cyclase inactive parathyroid hormone level is determined by subtracting the cyclase activating parathyroid hormone level from the total parathyroid hormone level.

10. The method of claim 1, wherein the cyclase activating parathyroid hormone level is compared with the total parathyroid hormone level.

11. The method of claim 1, wherein the cyclase inactive parathyroid hormone level is compared with the total parathyroid hormone level.

12. The method of claim 1, wherein the cyclase activating parathyroid hormone level is compared with the cyclase inactive parathyroid hormone level in the form of a ratio or proportion.

13. The method of claim 1 wherein the hyperparathyroidism is caused by chronic renal failure.

14. The method of claim 1 wherein the cyclase activating parathyroid hormone level and the cyclase inactive parathyroid hormone level are determined using an immunoassay.

15. The method of claim 14 wherein the cyclase activating parathyroid hormone level is determined using an antibody that distinguishes cyclase activating parathyroid hormone from cyclase inactive parathyroid hormone.

16. The method of claim 14 wherein the cyclase inactive parathyroid hormone level is determined using an antibody that distinguishes cyclase activating parathyroid hormone from cyclase inactive parathyroid hormone.

17. The method of claim 1, wherein the therapeutic treatment for hyperparathyroidism is vitamin D or vitamin D analogue treatment, calcium treatment, or calcimimetic administration.

18. The method of claim 17 wherein the Vitamin D analogue is paricalcitrol or calcitriol.

19. The method of claim 1 further comprising monitoring for vascular calcification in said patients.

20. The method of claim 19 wherein vascular calcification is monitored by monitoring alkaline phosphatase levels.

21. The method of claim 3 wherein the time sufficient to allow the patient to return to at least a relatively non-suppressed state is between about two weeks to about six weeks.

22. The method of claim 3 wherein the time sufficient to allow the patient to return to at least a relatively non-suppressed state is about four weeks.

23. The method of claim 1, wherein the cyclase inactive parathyroid hormone is a peptide having an amino acid sequence from between $PTH_{2-84}$ (SEQ ID NO:2) and $PTH_{34-84}$ (SEQ ID NO:3) and functions in vivo as a parathyroid hormone antagonist or inhibitor.

24. The method of claim 1, wherein the cyclase inactive parathyroid hormone is a peptide having an amino acid sequence of human $PTH_{7-84}$.

25. The method of claim 1, wherein the cyclase activating parathyroid hormone is a peptide having an amino acid sequence of human $PTH_{1-84}$.

* * * * *

SEQUENCE LISTING

```
<160> NUMBER OF SEQ ID NOS: 3

<210> SEQ ID NO 1
<211> LENGTH: 84
<212> TYPE: PRT
<213> ORGANISM: human parathyroid hormone peptide fragment

<400> SEQUENCE: 1

Ser Val Ser Glu Ile Gln Leu Met His Asn Leu Gly Lys His Leu
1               5                  10                  15

Asn Ser Met Glu Arg Val Glu Trp Leu Arg Lys Lys Leu Gln Asp
                20                  25                  30

Val His Asn Phe Val Ala Leu Gly Ala Pro Leu Ala Pro Arg Asp
                35                  40                  45

Ala Gly Ser Gln Arg Pro Arg Lys Lys Glu Asp Asn Val Leu Val
                50                  55                  60

Glu Ser His Glu Lys Ser Leu Gly Glu Ala Asp Lys Ala Asp Val
                65                  70                  75

Asn Val Leu Thr Lys Ala Lys Ser Gln
                80

<210> SEQ ID NO 2
<211> LENGTH: 83
```

```
-continued

<212> TYPE: PRT
<213> ORGANISM: human parathyroid hormone peptide fragment

<400> SEQUENCE: 2

Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
                20                  25                  30

His Asn Phe Val Ala Leu Gly Ala Pro Leu Ala Pro Arg Asp Ala
                35                  40                  45

Gly Ser Gln Arg Pro Arg Lys Lys Glu Asp Asn Val Leu Val Glu
                50                  55                  60

Ser His Glu Lys Ser Leu Gly Glu Ala Asp Lys Ala Asp Val Asn
                65                  70                  75

Val Leu Thr Lys Ala Lys Ser Gln
                80

<210> SEQ ID NO 3
<211> LENGTH: 51
<212> TYPE: PRT
<213> ORGANISM: human parathyroid hormone peptide fragment

<400> SEQUENCE: 3

Phe Val Ala Leu Gly Ala Pro Leu Ala Pro Arg Asp Ala Gly Ser
1               5                   10                  15

Gln Arg Pro Arg Lys Lys Glu Asp Asn Val Leu Val Glu Ser His
                20                  25                  30

Glu Lys Ser Leu Gly Glu Ala Asp Lys Ala Asp Val Asn Val Leu
                35                  40                  45

Thr Lys Ala Lys Ser Gln
                50
```